(12) United States Patent
Becker et al.

(10) Patent No.: US 7,611,256 B2
(45) Date of Patent: Nov. 3, 2009

(54) ILLUMINATOR FOR MEDICAL USE

(75) Inventors: Arie Becker, Kibbutz Afikim (IL); Simon Rothenstein, Rosh HaAyin (IL)

(73) Assignee: Medic.NRG Ltd., Kibbutz Afikim (IL)

( * ) Notice: Subject to any disclaimer, the term of this patent is extended or adjusted under 35 U.S.C. 154(b) by 0 days.

(21) Appl. No.: 11/974,261

(22) Filed: Oct. 12, 2007

(65) Prior Publication Data
US 2009/0097270 A1    Apr. 16, 2009

(30) Foreign Application Priority Data
Oct. 15, 2006  (IL) ..................... 178528
Feb. 22, 2007  (IL) ..................... 181498

(51) Int. Cl.
*A61B 1/01* (2006.01)
(52) U.S. Cl. .............. 362/119; 362/120; 362/109
(58) Field of Classification Search ........ 362/109, 362/120, 573, 581, 119
See application file for complete search history.

(56) References Cited

U.S. PATENT DOCUMENTS

| 3,919,541 A * | 11/1975 | Chao ................ 362/120 |
| 5,348,470 A | 9/1994 | McGowan et al. |
| 6,428,180 B1 * | 8/2002 | Karram et al. ........... 362/119 |
| 7,066,734 B1 | 6/2006 | Cooper |
| 7,393,114 B2 * | 7/2008 | Devlin .................. 362/109 |
| 2008/0261172 A1 * | 10/2008 | Rauchenzauner et al. ... 433/132 |
| 2009/0097270 A1 * | 4/2009 | Becker et al. ............. 362/573 |

FOREIGN PATENT DOCUMENTS

| DE | 29 25 051 A1 | 6/1979 |
| DE | 203 13 035 U1 | 8/2003 |
| EP | 1 093 765 A | 10/2000 |
| GB | 2 261 869 A | 11/1992 |
| GB | 2 414 811 A | 6/2004 |

* cited by examiner

*Primary Examiner*—Anabel M Ton
(74) *Attorney, Agent, or Firm*—Eckert Seamans Cherin Mellott, LLP

(57) ABSTRACT

An illuminator for medical instruments includes a first body part having, at one end, an instrument coupling head and a lighting element and, at its other end, a first electrical connector releasably attachable to a second, compatible electrical connector of a power source.

16 Claims, 4 Drawing Sheets

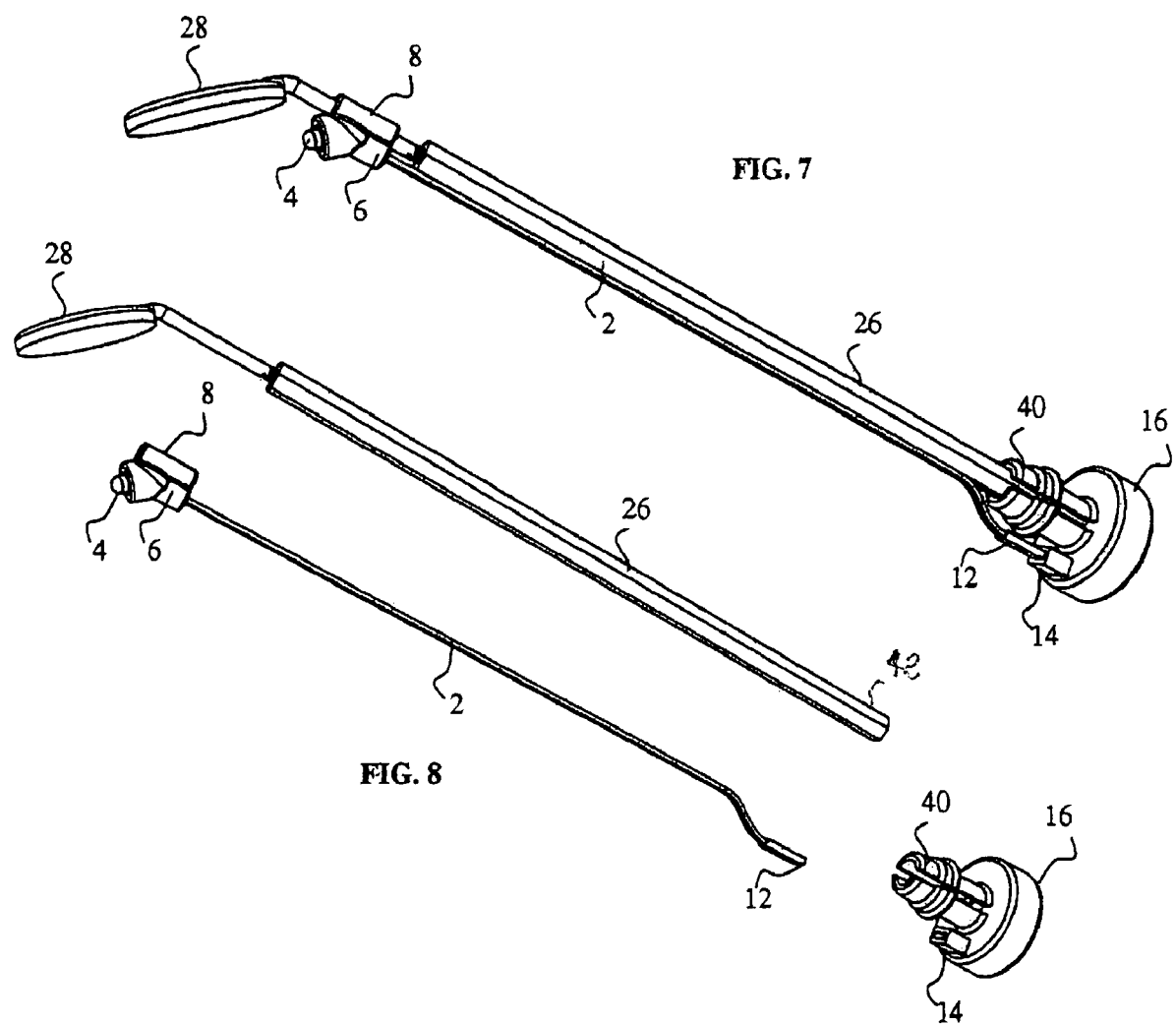

ILLUMINATOR FOR MEDICAL USE

BACKGROUND OF THE INVENTION

The present invention relates to illuminators and more particularly to illuminators for medical equipment, specifically to intra-oral dental equipment.

The common type of illuminator is the projector-type, wherein a light bulb is mounted on a moveable arm, which is affixed at one end to a base or a stationary surface. Such an illuminator, while being simple and effective for general use, is not suitable for illuminating specific body areas of a medically treated patient. This is so, since such an illuminator is stationarily located behind the person administering the treatment and the hand manipulating a tool is disposed between the light beam and the treated area, thus shadowing the area. While this situation could be remedied by constantly moving the arm of the illuminator to change the angle of the light beam, obviously this is very irritating during treatment, not to mention destructive and medically undesirable.

With a view to overcome the drawbacks of this basic type of an illuminator, there were devised other types of illuminators such as, small illuminators attached to the eyeglasses or head of the person administering the treatment or a light-converging reflecting mirror attached to the head of the person administering the treatment, reflecting light emanating from a source in front of the person administering the treatment. These solutions suffer from various disadvantages including the inaccuracy of the light beam which is supposed, at all times, to focus on and illuminate the treated area, namely, the necessity of the head of the person administering the treatment to be stationarily disposed at a certain angle with respect to the treated area during treatment, which, to say the least, is very awkward to the person administering the treatment.

Finally, there exist various medical instruments such as e.g., laryngoscopes, which are equipped with built-in illuminators, however, these instruments are expensive and intended for very long term use and not all of such instruments can be properly disinfected in autoclaves in their entirety, as actually required.

SUMMARY OF THE INVENTION

It is therefore a broad object of the present invention to overcome the drawbacks of the above-described illuminators for medical uses and to provide a self-contained illuminator suitable to be coupled to a great number of medical instruments.

It is a further object of the present invention to provide a self-contained illuminator to which a medical instrument is attachable and partly detachable for the purpose of disinfection separately or together with the instrument.

It is yet a further object of the present invention to provide a self-contained illuminator to which a medical instrument is attachable and partly detachable for the purpose of disinfection, separately or together with the instrument, wherein the instrument can be adjusted with respect to the lighting element.

In accordance with the invention there is therefore provided an illuminator for medical instruments, comprising a first body part having, at one end, an instrument coupling head and a lighting element, and at its other end, a first electrical connector releasably attachable to a second, compatible electrical connector of a power source.

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

FIG. 7 is a perspective view of a second embodiment of an illuminator according to the present invention, in its assembled operational state, as used with a dental instrument;

FIG. 8 shows perspective views of the illuminator of FIG. 7 in its disassembled non-operational state;

DETAILED DESCRIPTION OF THE PREFERRED EMBODIMENTS

Figure 1:
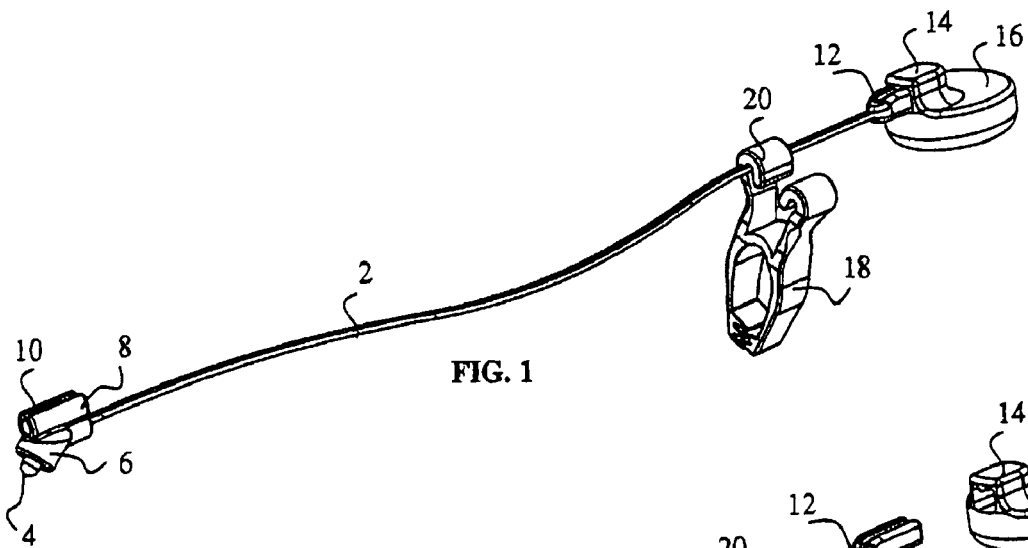
FIG. 1 is a perspective view of an embodiment of an illuminator according to the present invention, in its operational state.

Referring now to the drawings, there is illustrated in FIG. 1 an embodiment of an illuminator according to the present invention, in its operational state. The illuminator is composed of an electrical cable 2 having at one end a lighting element 4, e.g., a LED, preferably embedded in a housing 6 and integrally made with a coupling head 8 to which a medical instrument (not shown) can be coupled. The cable 4, the housing 6 and the coupling head 8 are advantageously made of a material capable of withstanding high temperatures without being damaged, e.g., high quality plastic material, in order to endure disinfection in an autoclave, without being damaged. Also, the housing 6 and the coupling head 8 are of a small size so as to fit and easily be manipulatable in the mouth of a patient. In the embodiment shown, the coupling head 8 is tubular, having a slot 10 extending along its length, so as to form flexible lips for facilitating easy engagement and disengagement of a medical instrument, usually the handle of such an instrument.

Figure 2:
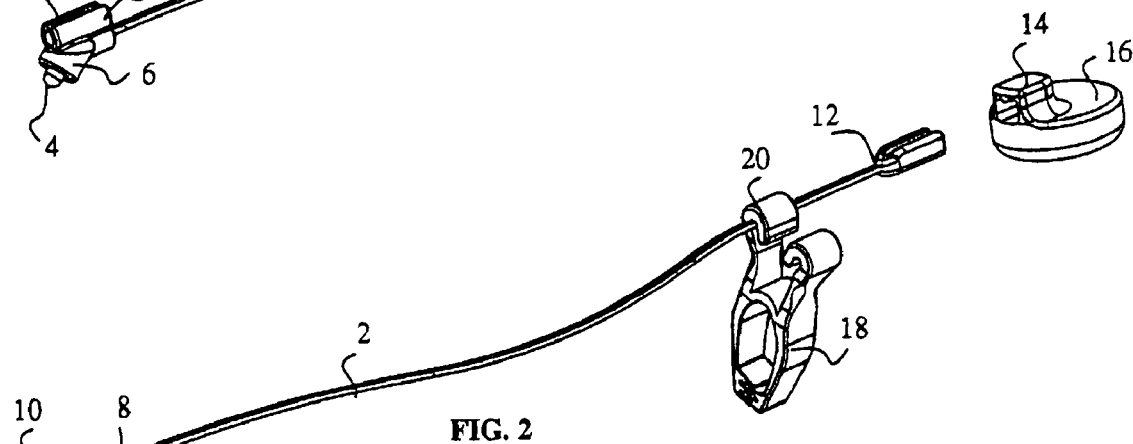
FIG. 2 is a perspective view of the illuminator of FIG. 1 in its non-operational state.

Referring now also to FIG. 2, there is affixed at the other end of the cable 4, an electrical plug 12, configured to be inserted into an electrical socket 14 attached to a power source, e.g., a housing 16 containing one or more batteries for lighting the LED. Also seen in the Figure is a clip 18 wedged onto or attached to the cable 4 by a connecting lug 20. The clip 18 is used to optionally attach the illuminator to an apron covering a patient during a medical or dental procedure, or directly to the patient's clothing, or for that matter, to any other convenient and suitable place. Obviously, such a clip 18 is also made of a durable material capable of withstanding high temperatures for the purpose of disinfection in an autoclave.

It should be noted that while an ON/OFF switch could be introduced on the lighting element's housing or on the cable, such a switch is purposely not added so as to remind the user to disengage the battery housing 16 from the cable 4 prior to inserting the illuminator into an autoclave for disinfection.

Figure 3:
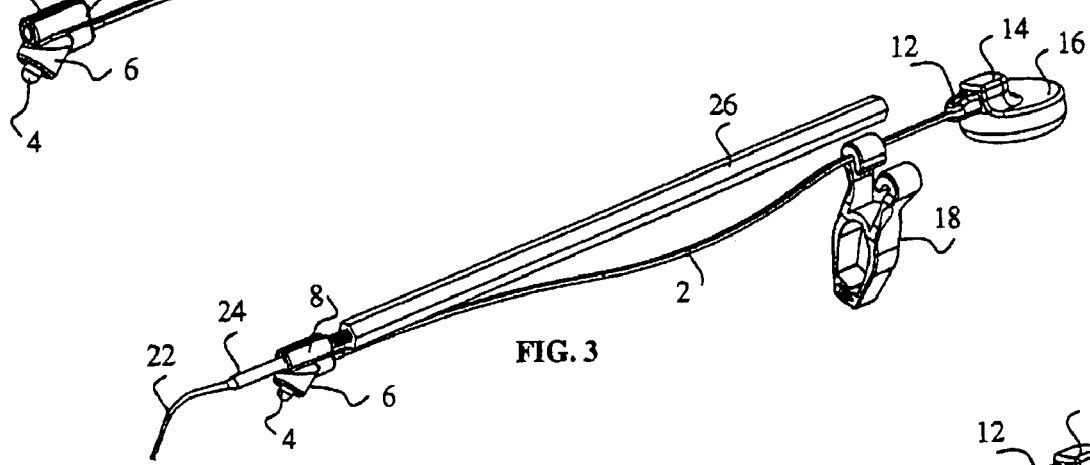
FIGS. 3 to 5 are perspective views of the illuminator according to the present invention, in its operational state, as attached to three different dental instruments.
Figure 4:
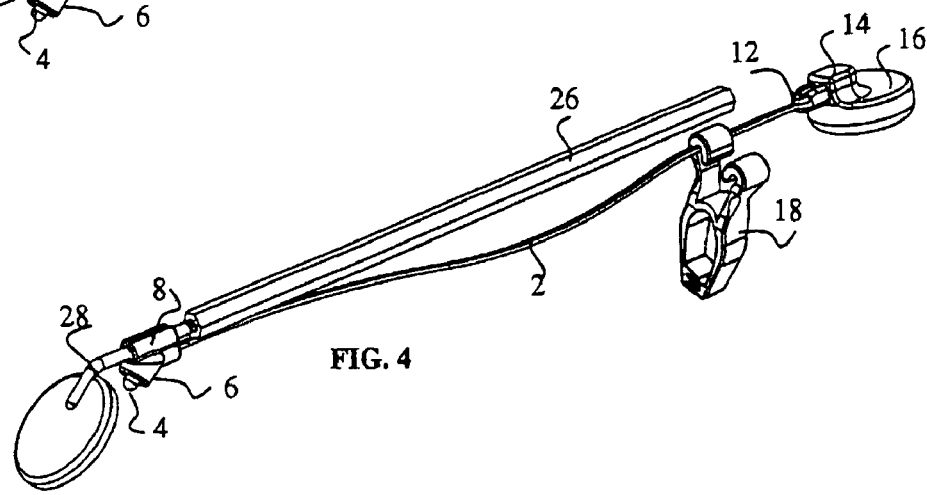
Figure 5:
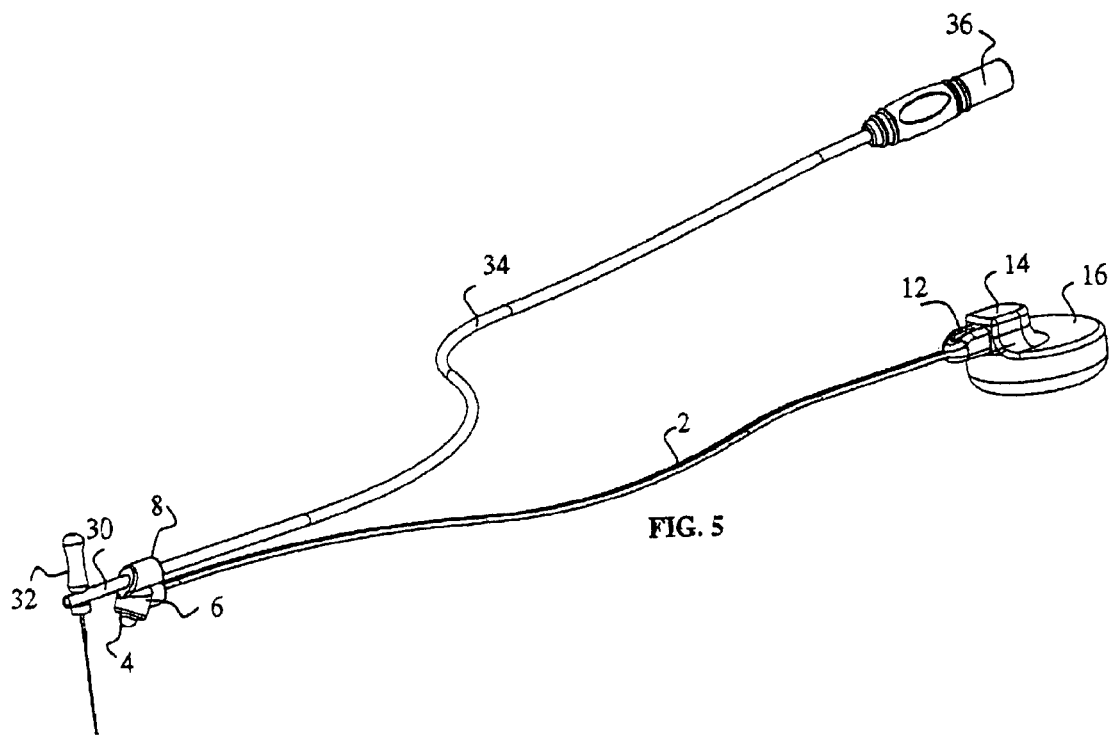

FIGS. 3 to 5 illustrate the illuminator as attached to various dental instruments. In FIG. 3 there is shown a tooth scaler 22 to which the illuminator is attached. In this embodiment, the coupling head 8 is made without a slot and the handle portion 24 of the scaler is inserted into the bore of the tubular coupling head 8 and held therein by pressure fit. Optionally, a longer manipulating handle portion 26 can then be screwed onto the handle portion 24.

Figure 6:
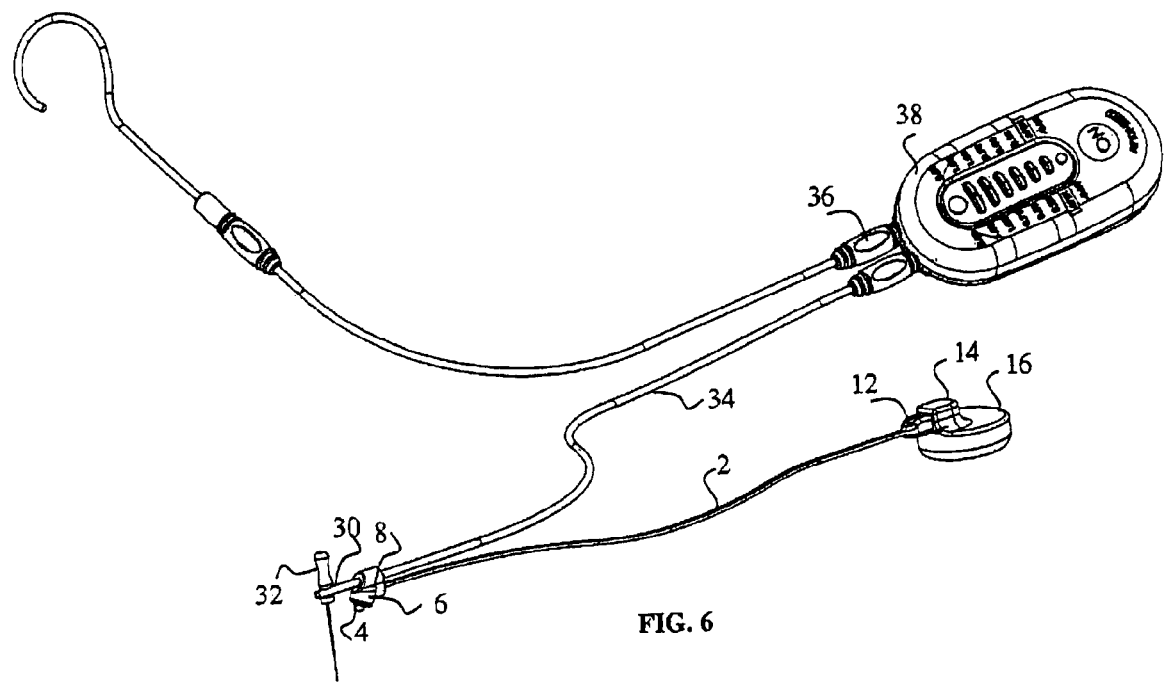
FIG. 6 is a perspective view of the illuminator according to the present invention as assembled with a dental file and an apex locator.

A similar arrangement is shown in FIG. 4. Here, the dental instrument is a mouth mirror 28. FIG. 5 illustrates the illuminator as affixed onto a coupling device 30 of a dental file 32. The device 30 and file 32 are electrically connected and lead via a cable 34 to a plug 36. The entire arrangement of a dental file 32, to which an illuminator is coupled, and leads to, a per se known apex locator 38, is shown in FIG. 6.

A modification of the embodiment of the illuminator shown in FIGS. 1 to 6 is illustrated in FIGS. 7 and 8. The battery housing 16 of the illuminator affixed onto a mouth mirror 28, is provided, in addition to the electrical socket 14, also with a socket 40, preferably a split-housing socket, configured to be detachably attached by press-fitting to an end part 42 of the handle portion 26.

In both embodiments, the battery housing and its sockets are detached from the cable 4 prior to disinfecting the remaining part of the illuminator in an autoclave.

Figure 9:
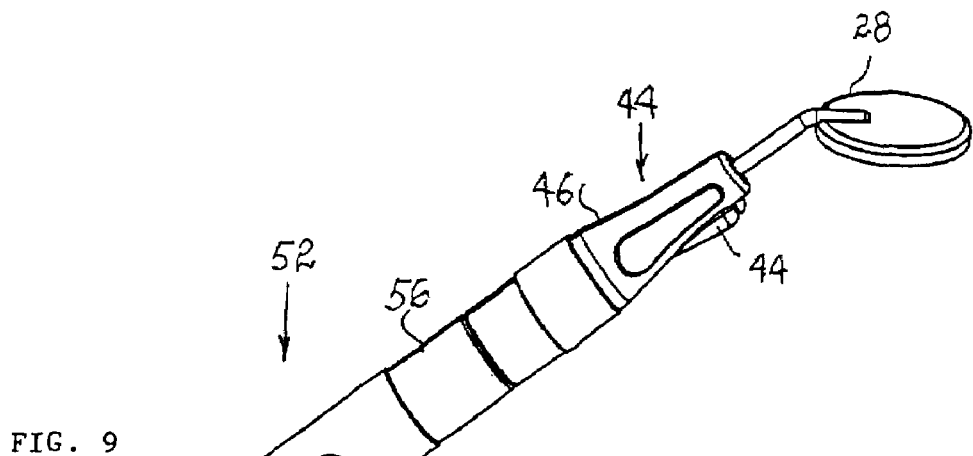
FIG. 9 is an isometric view of another embodiment of the illuminator, according to the present invention, in its assembled state.
Figure 10:
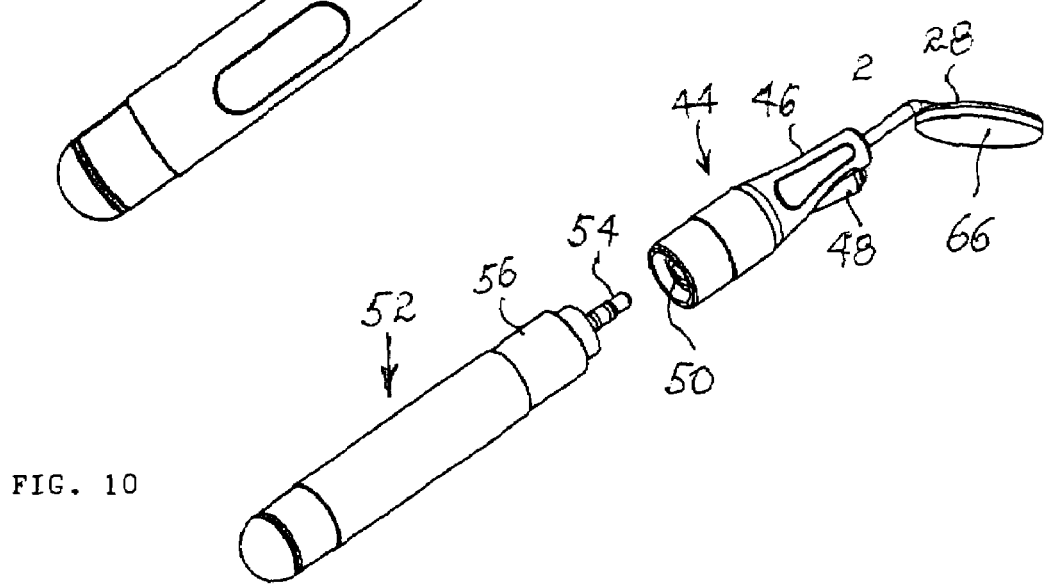
FIG. 10 is an isometric view of the illuminator of FIG. 9 showing the two housing parts in their detached state.
Figure 11:
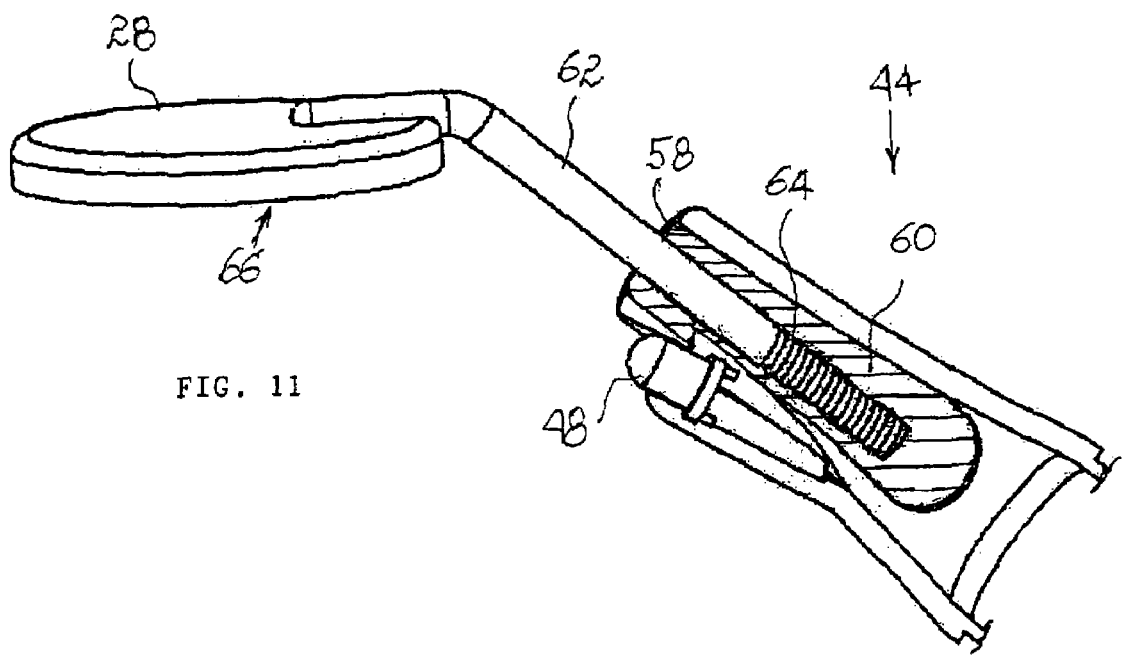
FIG. 11 is an enlarged partial cross-sectional view of the coupling head of the illuminator of FIGS. 9 and 10.

FIGS. 9 to 11 illustrate a further embodiment of the invention in which the illuminator is configured as a single rigid unit in use, easily detachable to form two separate parts, a first body part 44 including a coupling head 46, to which a medical instrument such as a mouth mirror 28, a tooth scaler or the like (not shown), can be affixed, a lighting element 48, e.g., a LED and an electrical connector 50. The unit further comprises a second body part 52 housing a power source, e.g., a regular or a rechargeable battery and an electrical connector 54. It should be readily understood that the first housing part 44 could be furnished with a male-type electrical connector while the second body part 52, with a compatible, female-type electrical connector. Advantageously, the second body part 52 may also include a power control circuit 56 for controlling the current fed to the lighting element 48, for keeping it steady.

Referring to FIG. 11, there is illustrated a cross-sectional view of the coupling head 44, showing a mirror 28 attached thereto during use. The coupling head 44 is made with a cavity 58 lined with a sleeve-like, elastic material 60, e.g., rubber. The connecting section 62 of mirror 28 may typically have a threaded portion 64, facilitating the attachment of the mirror to the coupling head 44 by screwing. Contrary, however, to other like instruments in which the mirror is attached by screwing, the connecting section of the mirror is simply stuck into the elastic material 60 and held therein by friction, without the need to tediously screw it in. A further advantage of the coupling head according to the present invention resides in the fact that by sticking in the mirror, as opposed to screwing it in, the reflecting surface 66 of the mirror 28 can be positioned at any desired axial distance from the lighting element 48 and angularly adjusted with respect to the light beam emerging from the element 48, so as to reflect the light onto the treated working location, without detracting from proper steady connection. This is achieved by the coupling material, e.g., rubber, which adequately grips the connecting section 62 of the mirror, even when the connecting section 62 is not completely stuck in.

Hence, the embodiment of FIGS. 9 to 11 not only facilitates the dismantling of the power source and medical instrument from the coupling head, but allows the disinfection of the coupling head which also contacts a patient's mouth, and furthermore allows the adjustment of the medical instrument with respect to the lighting element, so as to provide optimal lighting on the treated location, without interfering with the operator's view.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An illuminator for medical instruments, comprising:
a lamp housing having, at one end, an instrument coupling head and a lighting element, and at its other end, a first electrical connector releasably attachable to a second, compatible electrical connector of a power source, wherein:
the cable, the lamp housing and the coupling head are formed of a material capable of withstanding high temperatures,
the coupling head comprises a bore lined with elastic material and is configured for easy engagement and disengagement of a plurality of different medical instruments,
the medical instrument includes a connecting section and an effective section, and said material facilitates insertion of the connecting section to a predetermined depth and its rotation thereabout.

2. The illuminator as claimed in claim 1, wherein said first electrical connector includes a cable.

3. The illuminator as claimed in claim 1, wherein said second electrical connector comprises a power housing for accommodating said power source.

4. The illuminator as claimed in claim 1, wherein said coupling head is configured to be coupled to a medical instrument by pressure fit.

5. The illuminator as claimed in claim 1, wherein said medical instrument is a dental instrument and said lamp housing and coupling head are sized to easily fit and be manipulated in a mouth of a patient.

6. The illuminator as claimed in claim 5, wherein said dental instrument is selected from the group of dental instruments, including a mouth mirror, a scaler, a file or a file coupler.

7. The illuminator as claimed in claim 1, wherein said coupling head is a slotted tube.

8. The illuminator as claimed in claim 1, wherein said elastic material is formed as a closed-end sleeve.

9. The illuminator as claimed in claim 8, wherein said elastic material is rubber.

10. The illuminator as claimed in claim 1, wherein said power source comprises at least one battery enclosed in said lamp housing.

11. The illuminator as claimed in claim 3, wherein said power housing includes a control circuit for controlling the current applied to the lighting element.

12. The illuminator as claimed in claim 1, wherein said light element is a LED.

13. The illustrator as claimed in claim 1, wherein said lighting element and coupling head are made integrally.

14. The illuminator as claimed in claim 1, further comprising a clip wedged onto or attached to the cable for temporarily affixing the illuminator to a patient's apron, used during procedure.

15. An illuminator for medical instruments, comprising:
a housing having, at one end, an instrument coupling head and a lighting element, and at its other end, a first electrical connector releasably attachable to a second, compatible electrical connector of at least one battery enclosed in the housing, wherein:
the coupling head comprises a bore lined with elastic material and is configured for easy engagement and disengagement of a plurality of different medical instruments,
each medical instrument includes a connecting section and an effective section, and said material facilitates insertion of the connecting section to a predetermined depth and its rotation thereabout.

16. An illuminator for dental instruments, comprising:
a housing having, at one end, an instrument coupling head and a lighting element, and at its other end, a first electrical connector releasably attachable to a second, compatible electrical connector of a power source;
said housing and coupling head being sized to easily fit and be manipulated in a mouth of a patient, wherein:
the coupling head comprises a bore lined with elastic material and is configured for easy engagement and disengagement of a plurality of different medical instruments,
each medical instrument includes a connecting section and an effective section, and said material facilitates insertion of the connecting section to a predetermined depth and its rotation thereabout.

* * * * *